United States Patent
Kluge et al.

(10) Patent No.: US 10,617,786 B2
(45) Date of Patent: Apr. 14, 2020

(54) ADHESIVE ARTICLE COMPRISING A POLY(METH)ACRYLATE-BASED PRIMER LAYER AND METHODS OF MAKING SAME

(71) Applicant: 3M INNOVATIVE PROPERTIES COMPANY, Saint Paul, MN (US)

(72) Inventors: Bruce D. Kluge, Somerset, WI (US); Junkang J. Liu, Woodbury, MN (US); Robin E. Wright, Hudson, WI (US); Timothy M. Dietz, Mendota Heights, MN (US); Melissa A. Iseminger, Blaine, MN (US); Margaux B. Mitera, New Richmond, WI (US); Daniel O. Manalo, Oakdale, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 15/533,735

(22) PCT Filed: Dec. 9, 2015

(86) PCT No.: PCT/US2015/064605
§ 371 (c)(1),
(2) Date: Jun. 7, 2017

(87) PCT Pub. No.: WO2016/100021
PCT Pub. Date: Jun. 23, 2016

(65) Prior Publication Data
US 2017/0362470 A1   Dec. 21, 2017

Related U.S. Application Data

(60) Provisional application No. 62/094,094, filed on Dec. 19, 2014.

(51) Int. Cl.
*A61L 15/58* (2006.01)
*C09J 7/50* (2018.01)
(Continued)

(52) U.S. Cl.
CPC ............... *A61L 15/58* (2013.01); *C08L 83/06* (2013.01); *C09D 183/06* (2013.01); *C09J 7/385* (2018.01);
(Continued)

(58) Field of Classification Search
CPC .... C09J 7/50; C09J 2483/003; C09J 2483/00; C09J 2433/003; C09J 7/0257; A61L 15/58
See application file for complete search history.

(56) References Cited

U.S. PATENT DOCUMENTS 2,532,011 A   11/1950 Dahlquist
2,607,711 A   8/1952 Hendricks
(Continued)

FOREIGN PATENT DOCUMENTS

EP   1737504   1/2007
JP   07292320 A * 11/1995
(Continued)

OTHER PUBLICATIONS

Dohler, "RC Silicones for The Next Millennium", 1999, pp. 1-6.
(Continued)

*Primary Examiner* — Scott R. Walshon
(74) *Attorney, Agent, or Firm* — 3M Innovative Properties Company; Trisha D. Adamson

(57) ABSTRACT

An adhesive article comprising a poly(meth)acrylate-based primer layer and methods of making same. The article can include a backing, a primer layer located on a first major surface of the backing, and a silicone-based adhesive located on the primer layer. The primer layer can be derived from a primer precursor comprising poly(meth)acrylate functionalities. The method can include applying a primer precursor onto a first major surface of a backing, the primer precursor comprising a compound comprising poly(meth)acrylate
(Continued)

functionalities; irradiating the primer precursor; applying an adhesive on the irradiated primer precursor; and irradiating the adhesive and the irradiated primer precursor to form a primer layer located between the adhesive and the first major surface of the backing.

10 Claims, 1 Drawing Sheet

(51) Int. Cl.
*C09D 183/06* (2006.01)
*C08L 83/06* (2006.01)
*C09J 7/38* (2018.01)

(52) U.S. Cl.
CPC ........... *C09J 7/50* (2018.01); *C09J 2433/003* (2013.01); *C09J 2483/00* (2013.01); *C09J 2483/003* (2013.01)

(56) References Cited

U.S. PATENT DOCUMENTS

| | | | |
|---|---|---|---|
| RE24,906 E | 12/1960 | Ulrich | |
| 3,318,852 A | 5/1967 | Dixon | |
| 3,389,827 A | 6/1968 | Abere | |
| 3,502,497 A | 3/1970 | Crocker | |
| 4,112,213 A | 9/1978 | Waldman | |
| 4,133,938 A * | 1/1979 | Bingham | C04B 41/4988 |
| | | | 428/447 |
| 4,177,301 A * | 12/1979 | Smith, Jr. | B05D 7/02 |
| | | | 427/401 |
| 4,241,198 A | 12/1980 | Kobayashi | |
| 4,310,509 A | 1/1982 | Berglund | |
| 4,323,557 A | 4/1982 | Rosso | |
| 4,379,201 A | 4/1983 | Heilmann | |
| 4,595,001 A | 6/1986 | Potter | |
| 4,697,026 A * | 9/1987 | Lee | C08G 77/26 |
| | | | 556/418 |
| 4,728,571 A | 3/1988 | Clemens | |
| 4,737,410 A | 4/1988 | Kantner | |
| 5,032,460 A | 7/1991 | Kantner | |
| 5,202,190 A | 4/1993 | Kantner | |
| 5,214,119 A | 5/1993 | Leir | |
| 5,290,615 A | 3/1994 | Tushaus | |
| 5,356,706 A | 10/1994 | Shores | |
| 5,516,581 A | 5/1996 | Kreckel | |
| 5,750,630 A | 5/1998 | Sengupta | |
| 6,224,949 B1 | 5/2001 | Wright | |
| 7,332,227 B2 * | 2/2008 | Hardman | A61L 29/085 |
| | | | 428/447 |
| 7,442,442 B2 | 10/2008 | Strobel | |
| 2005/0249946 A1 | 11/2005 | Hsu | |
| 2008/0233348 A1 | 9/2008 | Ishiwatari | |
| 2013/0059105 A1 | 3/2013 | Wright | |

FOREIGN PATENT DOCUMENTS

| | | | |
|---|---|---|---|
| WO | WO 1995-06691 | 3/1995 | |
| WO | WO 2010-056541 | 5/2010 | |
| WO | WO 2010-056543 | 5/2010 | |
| WO | WO 2010-056544 | 5/2010 | |
| WO | WO 2012-091742 | 7/2012 | |
| WO | WO-2013096530 A1 * | 6/2013 | ........... C09J 183/04 |
| WO | WO 2013-173588 | 11/2013 | |

OTHER PUBLICATIONS

Jacobine, "Photopolymerizable Silicone Monomers, Oligomers, and Resins", Radiation Curing Science and Technology, 1992, pp. 181-240.
International Search Report for PCT International Application No. PCT/US2015/064605, dated Mar. 18, 2016, 4 pages.

* cited by examiner

ADHESIVE ARTICLE COMPRISING A POLY(METH)ACRYLATE-BASED PRIMER LAYER AND METHODS OF MAKING SAME

CROSS REFERENCE TO RELATED APPLICATIONS

This application is a national stage filing under 35 U.S.C. 371 of PCT/US2015/064605, filed Dec. 9, 2015, which claims the benefit of U.S. Provisional Application No. 62/094,094, filed Dec. 19, 2014, the disclosures of which are incorporated by reference in their entirety herein.

FIELD

The present disclosure generally relates to an adhesive article comprising a poly(meth)acrylate-based primer layer for improving the adhesion of the adhesive to a backing, and methods of making same.

BACKGROUND

Silicone-based adhesive usage is increasing especially in the health care field due to robust skin adhesion, low trauma removal, good biocompatibility and high breathability. Silicone-based adhesives are generally inert, and therefore, can be compatible to drug in adhesive (as opposed to reservoir-based) constructions for transdermal drug delivery. Industrially, adhesives for low surface energy applications, broader temperature applications and longer weathering applications are also gaining strength, which may require silicone-based adhesives. However, many silicone-based adhesives do not have strong interactions with (i.e., adhesion to) backings or substrates, which can cause the silicone-based adhesive to delaminate from the backing, leaving a coating of the silicone-based adhesive on the skin and/or object to be adhered.

Thus, backings often need to be pretreated with a chemical priming treatment in order to be used in combination with a silicone-based adhesive. Such treatments can require additional processing steps, as well as one or more of organic solvents, catalysts and initiators (e.g., photo initiators).

Although many primer coating chemistries have been developed previously, many of the chemistries rely on —Si—O—C— bonds to promote adhesion between a backing and a silicone-based adhesive. Such —Si—O—C— covalent bonds are hydrolytically unstable and thus may result in unstable bond performance upon aging.

SUMMARY

The present disclosure generally relates to primer layer chemistries for achieving adhesion promotion of an adhesive (e.g., a silicone-based adhesive) to a backing through carbon-carbon (—C—C—) bonds, e.g., instead of —Si—O—C— bonds. The primer chemistries of present disclosure can also provide adhesion promotion via environmentally-friendly processes, i.e., in the absence of any organic solvents, catalysts, or initiators (e.g., photo initiators).

Some aspects of the present disclosure provide an adhesive article. The article can include a backing having a first major surface and a second major surface opposite the first major surface, and a primer layer located on the first major surface of the backing. The primer layer can be derived from a primer precursor, which can include a compound comprising poly(meth)acrylate functionalities. The adhesive article can further include a silicone-based adhesive located on the primer layer on the first major surface of the backing, such that the primer layer is located between the first major surface of the backing and the adhesive, e.g., to enhance the adhesion between the silicone-based adhesive and the backing.

Some aspects of the present disclosure provide a method of making an adhesive article. The method can include applying a primer precursor onto a first major surface of a backing, wherein the primer precursor comprises a compound comprising poly(meth)acrylate functionalities. The method can further include irradiating the primer precursor on the backing, and applying an adhesive on the irradiated primer precursor on the first major surface of the backing. The method can further include irradiating the adhesive and the irradiated primer precursor on the first major surface of the backing to form a primer layer located between the adhesive and the first major surface of the backing.

Other features and aspects of the present disclosure will become apparent by consideration of the detailed description and accompanying drawings.

DETAILED DESCRIPTION

Figure 1:
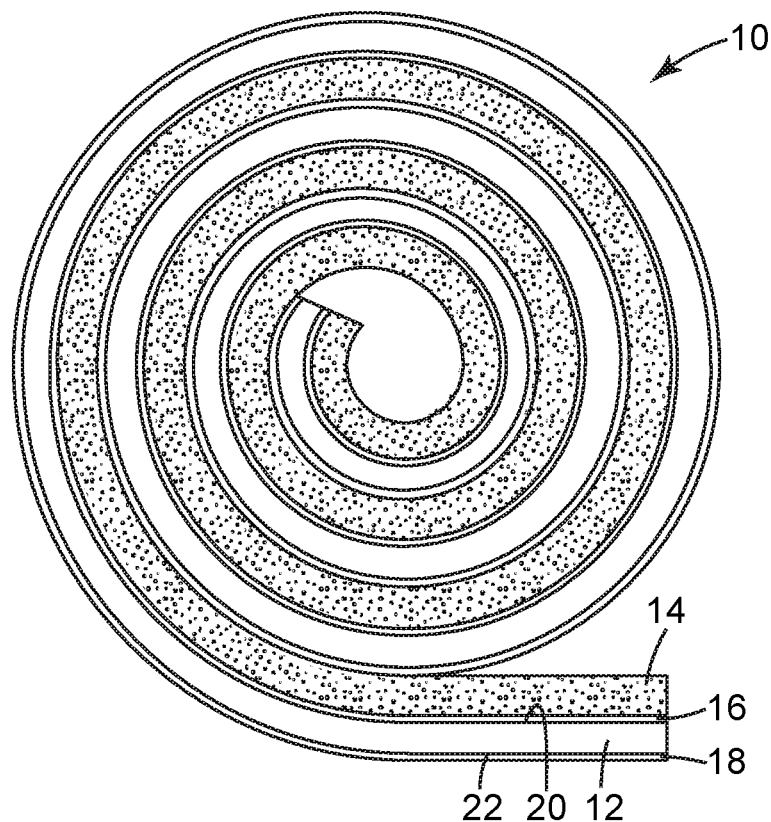
FIG. 1 is a schematic side cross-sectional view of an adhesive article according to one embodiment of the present disclosure.

The present disclosure generally relates to primer layer chemistries for achieving adhesion promotion of an adhesive (e.g., a silicone-based adhesive) to a backing through carbon-carbon (—C—C—) bonds, e.g., instead of —Si—O—C— bonds. The primer layer of the present disclosure can be derived from a primer precursor that includes one or more compounds comprising poly(meth)acrylate functionalities, such that the adhesive and the resulting primer layer are covalently bonded together (e.g., after at least partial cure) via carbon-carbon bonds. In some embodiments, the primer layer can be derived from a primer precursor comprising a poly(meth)acrylate siloxane, a non-siloxane poly(meth)acrylate, or a blend thereof.

Definitions

The term "a", "an", and "the" are used interchangeably with "at least one" to mean one or more of the elements being described.

The term "and/or" means either or both. For example "A and/or B" means only A, only B, or both A and B.

The terms "including," "comprising," or "having," and variations thereof, are meant to encompass the items listed thereafter and equivalents thereof as well as additional items.

Unless specified or limited otherwise, the terms "coupled" and variations thereof are used broadly and encompass both direct and indirect and couplings.

The terms "polymer" and "polymeric material" refer to both materials prepared from one monomer such as a homopolymer or to materials prepared from two or more monomers such as a copolymer, terpolymer, or the like. Likewise, the term "polymerize" refers to the process of making a polymeric material that can be a homopolymer, copolymer, terpolymer, or the like. The terms "copolymer" and "copolymeric material" refer to a polymeric material prepared from at least two monomers.

The terms "room temperature" and "ambient temperature" are used interchangeably to mean a temperature in the range of 20° C. to 25° C.

The terms "polychromatic UV radiation," "polychromatic UV light," "short wavelength polychromatic UV radiation," and "short wavelength polychromatic UV light," and variations thereof, all refer to ultraviolet radiation or light having an emission wavelength of 400 nm or less wherein the emission spectrum includes at least two intensity peaks, with at least one intensity peak occurring at no greater than 240 nanometers (nm).

The term "intensity peak" refers to a local maximum in an emission spectrum for a UV radiation source when plotted as emission intensity as a function of emission wavelength. The emission spectrum may have one or more intensity peaks over the wavelength range covered by the emission spectrum. Thus, an intensity peak need not correspond to the maximum emission intensity peak over the entire wavelength range covered by the emission spectrum.

The term "substantially inert atmosphere" refers to an atmosphere having an oxygen content of no greater than 500 ppm.

The term "(meth)acrylic" or "(meth)acrylic-functional" or "(meth)acrylate functionalities" includes materials that include one or more ethylenically unsaturated acrylic- and/or methacrylic-functional groups: e.g. -AC(O)C(R)=CH$_2$, preferably wherein A is O, S or NR; and R is a 1-4 carbon lower alkyl group, H or F.

The term "poly(meth)acrylate" is used to refer to a compound comprising three or more (meth)acrylate functionalities (i.e., greater than two (meth)acrylate functionalities).

The term "siloxane" includes any chemical compound composed of units of the form R$_2$SiO, wherein R is a hydrogen atom or a hydrocarbon group.

The phrase "substantially free of" when referring to a particular material or compound means that the particular material or compound is not intentionally added to a composition, or is not present in an "effective amount." As is well understood, an "effective amount" of a catalyst or initiator depends on a variety of factors, including the type of catalyst or initiator, the composition of the curable material, and the cure method. In some embodiments, a composition can be described as being "substantially free of" a material or compound if that material or compound is present in an amount in the composition of less than 5 wt %, in some embodiments, less than 1 wt %, in some embodiments, less than 0.5 wt %, in some embodiments, less than 0.1 wt %, in some embodiments, less than 0.05 wt %, and in some embodiments, less than 0.01 wt %.

Adhesive Articles

Figure 2:
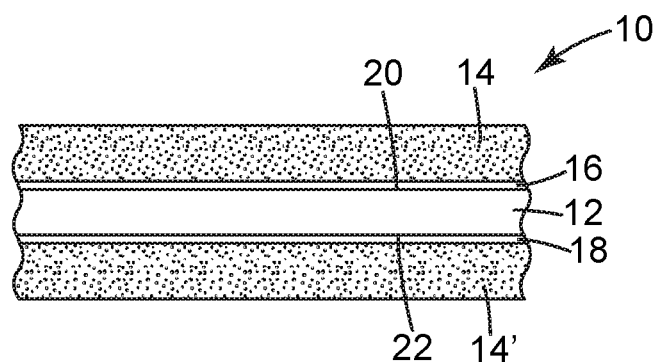
FIG. 2 is a close-up schematic side cross-sectional view of the adhesive article of FIG. 1.

FIGS. 1 and 2 illustrate an adhesive article 10 according to one embodiment of the present disclosure. As shown in FIG. 1, in some embodiments, the adhesive article 10 can be provided in rolled form and can include a backing 12, an adhesive 14, a primer layer 16, and optionally, a low-adhesion backsize (LAB) coating 18.

In some embodiments, the adhesive articles of the present disclosure can be used as medical articles. Generally, "medical articles" include, but are not limited to, medical tapes, surgical drapes, medical dressings (e.g., intravenous dressings, wound dressings, etc.), electrodes, ostomy pouches, transdermal drug delivery devices (e.g., patches), first aid bandages, and combinations thereof.

The backing 12 can include a first major surface 20 and a second major surface 22 opposite the first major surface 20. The adhesive 14 is shown a being coupled to the first major surface 20 of the backing 12, and the LAB coating 18 is shown as being coupled to the second major surface 22 of the backing 12. The primer layer 16 is shown as being located on the first major surface 20 of the backing 12, between the first major surface 20 of the backing 12 and the adhesive 14. That is, the primer layer 16 can be positioned to enhance or promote the adhesion between the adhesive 14 and the backing 12 (i.e., the first major surface 20 of the backing 12). The primer layer 16 can also be referred to as an "adhesive primer," "adhesive primer layer," "adhesion promoter," "adhesion promoter layer," or variations thereof.

As shown in FIG. 1, in embodiments in which the adhesive article 10 is provided in roll form, LAB coating 18 can be configured to provide release characteristics to the adhesive 14, such that the adhesive article 10 can be directly rolled upon itself without the use of a release liner. Alternatively, or additionally, the adhesive article 10 can include a release liner over the adhesive 14 that provides sufficient release characteristics to the adhesive 14.

FIG. 2 illustrates a schematic close-up view of the adhesive article 10 wound directly on itself without a release liner, showing the LAB coating 18 of a first portion of the adhesive article 10 serving as a release layer for the same adhesive 14' of a second portion of the adhesive article 10. Thus, as shown, the adhesion of the adhesive 14 to the first major surface 20 of the backing 12 can be promoted by the primer layer 16, and the adhesion of the adhesive 14 to the second major surface 22 of the backing can be limited or reduced by the LAB coating 18.

As a result, the adhesive 14 can have (i) a first adhesion strength on the LAB coating 18 on the second major surface 22 of the backing 12, and (ii) a second adhesion strength on the primer layer 16 on the first major surface 20 of the backing 12. The primer layer 16 can be configured, such that the first adhesion strength is less than (i.e., substantially less than) the second adhesion strength, and such that the adhesive 14 is not undesirably delaminated from the first major surface 20 of the backing 12.

As mentioned above and described in greater detail below, the primer layer 16 can be derived from a primer precursor comprising a compound comprising poly(meth)acrylate functionalities. In some embodiments, the primer precursor can include one or more compounds comprising poly(meth)acrylate-functional siloxanes. In some embodiments, the primer precursor can include one or more compounds comprising poly(meth)acrylate-functional non-siloxanes. In some embodiments, the primer precursor can include a blend or one or more poly(meth)acrylate-functional siloxanes and one or more poly(meth)acrylate-functional non-siloxanes (or "non-siloxane poly(meth)acrylates").

Methods of Making Adhesive Articles

Methods of making adhesive articles of the present disclosure can include applying a primer precursor onto a first major surface of a backing, irradiating the primer precursor on the backing (i.e., to at least partially cure the primer precursor), applying an adhesive on the irradiated primer precursor on the first major surface of the backing, and irradiating the adhesive and the irradiated primer precursor on the first major surface of the backing to form a primer layer located between the adhesive and the first major surface of the backing.

The primer precursor is therefore initially irradiated to at least partially cure the primer precursor. Because the final primer layer may not yet be fully cure or formed at this stage (i.e., prior to applying the adhesive), the primer precursor at this stage is referred to as the "irradiated primer precursor." After the adhesive is applied, the adhesive is irradiated to cure the adhesive and optionally to cure the primer precursor to form the primer layer. Thus, in some embodiments, the primer layer may not be fully formed (i.e., cured) until the adhesive is irradiated.

As described in greater detail below, the primer precursor can include a compound comprising poly(meth)acrylate functionalities, such that the resulting primer layer and the adhesive are covalently bonded together via carbon-carbon bonds, thereby promoting the adhesion between the adhesive and the backing via stable (i.e., —C—C—) bonds.

Applying the primer precursor and the adhesive can be accomplished by a variety of means, including, but not limited to, various coating methods, such as roll coating, spray coating, curtain coating, dip coating, gravure coating, bar coating, vapor coating, die coating, other suitable coating methods, or combinations thereof.

Irradiating the primer precursor and/or the adhesive can include irradiating with a variety of suitable radiation, including, but not limited to, one or more of ultraviolet (UV) radiation, electron beam (e-beam) radiation, gamma radiation, thermal or IR radiation, other suitable radiation, and combinations thereof.

In some embodiments, UV radiation can include short wavelength polychromatic UV radiation, as described above. Particular advantages can be obtained in embodiments employing primer precursor chemistries that are suitable for polychromatic UV radiation, such as avoiding the need for any catalysts or initiators to generate an initiating radical species. In some embodiments, irradiating can occur in a substantially inert atmosphere. In some embodiments, low-pressure mercury arc lamps, and/or a mercury amalgam lamps having enhanced short wavelength output at 185 nm, can serve as a source of short wavelength polychromatic UV radiation.

In some embodiments, short wavelength polychromatic ultraviolet light sources useful in the method of the present disclosure are those having output in the region from about 160 (+/−5) nm to about 240 (+/−5) nm, inclusive. In some embodiments of any of the foregoing, a peak intensity is at a wavelength between about 170 (+/−5) nm, 180 (+/−5) nm, or even 190 (+/−5) nm; to about 215 (+/−5) nm, 210 (+/−5) nm, 205 (+/−5) nm, or even 200 (+/−5) nm. In some particular exemplary embodiments, a peak intensity is at a wavelength of about 185 (+/−2) nm.

In some embodiments, the short wavelength polychromatic ultraviolet light source includes at least one low pressure mercury vapor lamp, at least one low pressure mercury amalgam lamp, at least one pulsed Xenon lamp, at least one glow discharge from a plasma emission source, or combinations thereof.

Additional details regarding using short wavelength polychromatic UV radiation, and suitable sources therefor, can be found in U.S. Publication No. 2013/0059105 (Wright et al.), which is incorporated herein by reference in its entirety.
Primer Layer and Primer Precursor As mentioned above, the primer layer can be derived from a primer precursor. The primer precursor can be formed of a variety of materials that include a compound comprising three or more (meth)acrylate functionalities (i.e., a poly(meth)acrylate-functional compound).

In some embodiments, the poly(meth)acrylate-functional compound can include a (meth)acrylate-functional siloxane having three or more (meth)acrylate functionalities, where the siloxane can be in the form of a monomer, an oligomer, a polymer, or combinations thereof.

Additionally, or alternatively, the primer precursor can include poly(meth)acrylate-functional non-siloxanes, i.e., monomers, oligomers and/or polymers having three or more (meth)acrylate functionalities. For example, in some embodiments, the primer precursor can include a tri-(meth)acrylate monomer.

In some embodiments, the primer precursor can include a blend of one or more poly(meth)acrylate-functional siloxanes and one or more poly(meth)acrylate-functional non-siloxanes. In some embodiments, the ratio (i.e., weight/weight, w/w) of poly(meth)acrylate-functional siloxanes to poly(meth)acrylate-functional non-siloxanes in the blend can be at least 75:25; in some embodiments, at least 80:20; in some embodiments, at least 85:15; in some embodiments, at least 90:10; and in some embodiments, at least 95:5.

Various (co)polymerizable poly(meth)acrylate-functional siloxanes are useful materials for preparing a primer layer according to the present disclosure. Such poly(meth)acrylate-functional siloxanes can be prepared by a variety of methods, generally through the reaction of chloro-, silanol-, aminoalkyl-, epoxyalkyl-, hydroxyalkyl-, vinyl-, or silicon hydride-functional polysiloxanes with a corresponding (meth)acrylate-functional capping agent. These preparations are reviewed in a chapter entitled "Photo(co)polymerizable Silicone Monomers, Oligomers, and Resins" by A. F. Jacobine and S. T. Nakos in Radiation Curing Science and Technology, (Plenum: New York, 1992), pp. 200-214.

Suitable poly(meth)acrylate-functional siloxane oligomers include those (meth)acryl-modified polylsiloxane resins commercially available from, for example, Goldschmidt Chemical Corporation (Evonik TEGO Chemie GmbH, Essen, Germany) under the TEGO™ RC designation. An example of a blend recommended for achieving balanced adhesion promotion and compatibility with the adhesive is a 70:30 (weight/weight, w/w) blend of TEGO RC902 and TEGO RC711.

In some exemplary embodiments, the primer precursor can include essentially only one or more (co)polymerizable (meth)acrylate-functional siloxane(s), and is substantially-free of other (co)polymerizable materials. Thus, in further exemplary embodiments of any of the foregoing, the primer precursor can include essentially one or more (meth)acrylate-functional siloxane monomers. In such exemplary embodiments, the primer precursor can consist essentially of one or more (meth)acrylate-functional siloxane oligomers. In other such exemplary embodiments, the primer precursor consists essentially of one or more (meth)acrylate-functional polysiloxanes.

Additional details regarding poly(meth)acrylate-functional siloxanes that can be employed in the primer precursors of the present disclosure are described in U.S. Publication No. 2013/0059105 (Wright et al.). Wright et al. state that ethylenically unsaturated free radically (co)polymerizable siloxanes, including especially the (meth)acrylate-functional siloxane oligomers and (co)polytners containing telechelic and/or pendant acrylate or methacrylate groups, are particularly useful precursor materials.

Suitable poly(meth)acrylate-functional non-siloxanes can include, but are not limited to, poly(meth)acrylate-functional monomers, oligomers and/or polymers, including, but not limited to, polyfunctional (meth)acrylate-functional free radically (co)polymerizable monomers include ester derivatives of alkyl diols, triols, tetrols, etc. (e.g., 1,4 butanediol di(meth)acrylate, 1,6-hexanediol di(meth)acrylate, trimethylolpropane tri(meth)acrylate, and pentaerythritol tri(meth)acrylate). Polyfunctional (meth)acrylate and methacrylate monomers described in U.S. Pat. No. 4,379,201 (Heilmann et al.), such as 1,2-ethanediol di(meth)acrylate, 1,12-dodecanediol di(meth)acrylate, pentaerythritol tetr(meth)acrylate can also be used in the present disclosure.

Polyfunctional (meth)acrylates and including (meth)acrylated epoxy oligomers, (meth)acrylated aliphatic urethane oligomers, (meth)acrylated polyether oligomers, and (meth)acrylated polyester oligomers, such as those commercially available from UCB Radcure Inc, Smyrna, Ga. under the EBECRYL tradename, and those available from Sartomer, Exton, Pa., may also be employed.

Additional details regarding non-siloxane poly(meth)acrylates that can be employed in the primer precursors of the present disclosure are described in U.S. Publication No. 2013/0059105 (Wright et al.) and U.S. Pat. No. 6,224,949 (Wright et al.), which is also incorporated herein by reference in its entirety.

In some embodiments, the primer precursor can further include one or more (co)polymerizable starting materials, including, but not limited to, (i) one or more non-(meth)acrylate-functional siloxane monomers, oligomers and/or polymers (i.e., those that have other non-(meth)acrylate functionalities); (ii) (meth)acrylate-functional monomers, oligomers and/or polymers having mono-, di-, or poly-meth(acrylate) functionality; and combinations thereof. Additional details regarding various (co)polymerizable starting materials can be found in U.S. Publication No. 2013/0059105 (Wright et al.).

Examples of suitable non-(meth)acrylate-functional siloxane monomers, oligomers and/or polymers for use as optional (co)polymerizing materials in the primer precursor can include, but are not limited to, vinyl-functional polysiloxanes, hydroxyl-functional polysiloxanes, amine-functional polysiloxanes, hydride-functional polysiloxanes, epoxy-functional polysiloxanes, and combinations thereof. In some embodiments, the non-(meth)acrylate-functional polysiloxane material comprises from 0.1 to 95 wt %, inclusive, of the primer precursor. Additional details regarding non-(meth)acrylate functional siloxanes that can be employed can be found in U.S. Publication No. 2013/0059105 (Wright et al.).

Examples of (meth)acrylate-functional monomers, oligomers and/or polymers having mono-, di-, or poly-meth(acrylate) functionality that can be employed as (co)polymerizing materials include those described above with respect to poly(meth)acrylate-functional non-siloxanes, as well as any of the mono- and di-functional (meth)acrylate-functional monomers, oligomers and/or polymers described in U.S. Publication No. 2013/0059105 (Wright et al.) and U.S. Pat. No. 6,224,949 (Wright et al.).

As mentioned above, in some embodiments, the primer precursor can be substantially free of an organic solvent. In addition, in some embodiments, the primer precursor can be substantially free of any catalysts and initiators.

In some embodiments, the coating weight of the primer layer (or of the primer precursor) can be at least 0.04 g/m$^2$; in some embodiments, at least 0.05 g/m$^2$; in some embodiments, at least 0.1 g/m$^2$; in some embodiments, at least 0.15 g/m$^2$; in some embodiments, at least 0.2 g/m$^2$; and in some embodiments, at least 0.3 g/m$^2$. In some embodiments, the coating weight of the primer layer (or of the primer precursor) can be no greater than 5 g/m$^2$; in some embodiments, no greater than 4 g/m$^2$; in some embodiments, no greater than 3 g/m$^2$; in some embodiments, no greater than 2 g/m$^2$; in some embodiments, no greater than 1.5 g/m$^2$; in some embodiments, no greater than 1 g/m$^2$; and in some embodiments, no greater than 0.5 g/m$^2$.

In some embodiments, the primer precursor can be applied at a thickness of about 0.1 (+/−0.05) micrometer (μm) to about 5 (+/−0.1) μm. In some embodiments, the primer precursor can be applied at a thickness of about 0.4 (+/−0.05) μm to about 1 (+/−0.1).

Adhesives

Adhesives of the present disclosure can include pressure-sensitive adhesives, and particularly, pressure-sensitive adhesives that are suitable for use as a skin-contact adhesive.

Adhesives may be an acrylate, silicone, urethane, hydrogel, hydrocolloid, natural rubber, or synthetic rubber. Adhesion can also be tuned through changes in adhesive composition, adhesive thickness, or adhesive surface area (e.g., by employing a pattern-coated adhesive).

"Adhesion" (or "adhesion strength") refers to the force required to separate an adhesive from an underlying substrate. Adhesion can be measured in a number of ways. For example, adhesion can be defined by peel force or shear force. In some embodiments, adhesion can be defined by peel adhesion using ASTM D3330/D3330M-04(2010). In some embodiments, adhesion can be defined by shear adhesion using ASTM D3654M-06(2011). Adhesion is highly dependent on the specific substrate being adhered to, as well as the time the adhesive (e.g., pressure-sensitive adhesive) is allowed to dwell on the substrate.

For example, typical peel adhesion values exhibited by pressure-sensitive adhesives in adhesive articles maybe in the range of 20 to 300 g/cm as measured from stainless steel.

In some embodiments, the adhesive can include a silicone (or "silicone-based") adhesive or an acrylate (or "acrylate-based") adhesive, a synthetic rubber (or "synthetic rubber-based") adhesive, or combinations.

The term "acrylate" or "acrylate-based" or "acrylate-containing" refers to monomeric acrylic or methacrylic esters of alcohols. Acrylate and methacrylate monomers are referred to collectively herein as "acrylate" monomers. Materials that are described as "acrylate-based" or "acrylate-containing" contain, or are derived from, at least some acrylate monomers and may contain additional co-monomers.

The term "acrylic acid" or "acrylic acid-based" or "acrylic acid-containing" refers to monomers comprising acrylic acid. Acrylic acid monomers are referred to collectively herein as "acrylic acid" monomers. Materials that are described as "acrylic acid-based" or "acrylic acid-containing" contain, or are derived from, at least some acrylic acid monomers and may contain additional co-monomers. This class of adhesives can also fall within a broader class of acidic adhesives (i.e., adhesives comprising an acidic component), and in some embodiments, the adhesive can include an acidic adhesive, and particularly, an acrylic acid-based adhesive.

Suitable acrylate adhesives that can be applied to skin such as the acrylate copolymers are described in U.S. Pat. No. RE 24,906, the disclosure of which is hereby incorporated by reference. In particular, a 97:3 iso-octyl acrylate: acrylamide copolymer. Another acrylate adhesive is an 70:15:15 isooctyl acrylate:ethyleneoxide acrylate:acrylic acid terpolymer, as described in U.S. Pat. No. 4,737,410 (Example 31), the disclosure of which is hereby incorporated by reference. Other useful acrylate adhesives are described in U.S. Pat. Nos. 3,389,827, 4,112,213, 4,310,509, and 4,323,557, the disclosures of which are incorporated herein by reference.

The term "silicone" or "silicone-based" or "silicone-containing" refers to polymers that contain units with dialkyl or diaryl siloxane (—SiR$_2$O—) repeating units. The silicone-based polymers are substantially free of hydrocarbon segments. The terms silicone and siloxane are used interchangeably.

Generally, silicone adhesives are able to effectively secure materials or substrates to skin and upon removal from the skin produce little or no skin damage.

Suitable silicone adhesives can include nonfunctionalized polysiloxanes, such as polydimethylsiloxane (PDMS). Suitable silicone adhesives can also include silicone adhesives configured to be cured by any of the above-described radiations.

Examples of suitable silicone adhesive systems can include, but are not limited to, products available under the following trade designations: Dow Corning MG 7-9850, Wacker SILPURAN® 2110 and 2130, Bluestar SILBIONE® RT Gel 4317 and 4320, Nusil MED-6345 and 6350. Other examples of suitable silicone adhesives are disclosed in PCT Publications WO2010/056541, WO2010/056543 and WO2010/056544, the disclosures of which are incorporated herein by reference.

The term "synthetic rubber adhesive" or "synthetic rubber-based adhesive" refers to an adhesive composed from a group of synthetic rubbers or any desired blend of synthetic rubbers, it being possible to select the synthetic rubber or synthetic rubbers from the group of random, branch, or block copolymerized styrene-butadiene rubbers (SBR), butadiene rubbers (BR), synthetic polyisoprenes (IR), butyl rubbers (BlR), halogenated butyl rubbers (XBlR), ethylene-vinyl acetate (EVA) copolymers and polyurethanes and/or blends thereof.

Examples of suitable synthetic rubber adhesive systems can include, but are not limited to, adhesives made from styrene-isoprene-styrene (SIS) and styrene-butadiene-styrene (SBS).

For skin-contact adhesives, it is desirable that the adhesive is able to transmit moisture vapor at a rate greater to or equal to that of human skin. While such a characteristic can be achieved through the selection of an appropriate adhesive, it is also contemplated that other methods of achieving a high relative rate of moisture vapor transmission may be used, such as perforating the adhesive or pattern coating the adhesive, as described in U.S. Pat. No. 4,595,001 and U.S. Pat. App. Pub. 2008/0233348, the disclosures of which are incorporated herein by reference. In some embodiments, each of the adhesives can optionally be applied in a patterned or discontinuous manner.

Backings

Backings of the present disclosure can include single-layer and multi-layer constructions, and can be formed a polymer, an elastomer, a metal, glass, a ceramic, a composite material, or a combinations thereof. Useful backings can be in the form of foams (e.g., polymeric foams), films (e.g., polymeric films, metallic films or foils), fabrics (wovens), and nonwovens.

In some embodiments, backings of the present disclosure can include medical backings that are particularly suitable for use in medical articles, i.e., having have the proper breathable, optical, and mechanical properties.

Potentially useful polymeric backing materials are disclosed in U.S. Pat. No. 5,516,581 (Kreckel et al.) and PCT Publication No. WO 95/06691. Representative examples of potentially useful polymeric backing materials for polymeric foam layers or polymeric film layers include, but are not limited to, polyurethanes; polyesters, e.g., polyethylene terephthalate (PET); polyolefins, e.g., polyethylene, including high density polyethylene, low density polyethylene, linear low density polyethylene, and linear ultra low density polyethylene, polypropylene, polybutylenes, or combinations thereof (e.g., a polyethylene blend); vinyl copolymers, e.g., polyvinyl chlorides, both plasticized and unplasticized, polyvinyl acetates, or combinations thereof polyimides; polyamides; polystyrenes; cellulose acetate; olefin copolymers, e.g., ethylene/methacrylate copolymers, ethylene/vinylacetate copolymers, acrylonitrile-butadiene-styrene copolymers, ethylene/propylene copolymers, or combinations thereof; acrylic polymers and copolymers; and combinations thereof. Mixtures or blends of any plastic or plastic and elastomer materials, such as polypropylene/polyethylene, polyurethane/polyolefin, polyurethane/polycarbonate, and polyurethane/polyester, can also be used. Suitable films can also include metallic foils.

Foams can be selected to optimize tape properties such as conformability and resiliency, which are useful when the adhesive article is to be adhered to surfaces having surface irregularities, e.g., painted wallboard. Conformable and resilient polymeric foams are well suited for applications in which the adhesive article is to be adhered to surfaces having surface irregularities. Such is the case with a typical wall surface. Foam layers for use in the backing generally will have a density of about 2 to about 30 pounds per cubic foot (about 32 to about 481 kg/m$^3$).

Films may be used to increase load bearing strength and rupture strength of the adhesive article. Films are particularly well suited to applications involving adhering smooth surfaces together. A film backing, or layer thereof, can have a thickness of about 10 micrometers (0.4 mil) to about 254 micrometers (10 mils). Films can be continuous or perforated.

In some embodiments, the backing can be formed of an elastomeric material. Suitable elastomeric backing materials include, e.g., styrene-butadiene copolymer, polychloroprene (i.e., neoprene), nitrile rubber, butyl rubber, polysulfide rubber, cis-1,4-polyisoprene, ethylene-propylene terpolymers (e.g., EPDM rubber), silicone rubber, silicone elastomers such as silicone polyurea block copolymers, polyurethane rubber, polyisobutylene, natural rubber, acrylate rubber, thermoplastic rubbers, e.g., styrene-butadiene block copolymers and styrene-isoprene-styrene block copolymers, and thermoplastic polyolefin rubber materials.

Suitable nonwoven backings can be formed of a variety of materials, including, but not limited to, polyesters, polyurethanes, polyimides, polyamides, polystyrenes, cellulose, polyolefins, glass fibers, ceramic fibers, and combinations thereof.

Suitable fabric backings can be formed of a variety of materials, including, but not limited to, polyesters, polyurethanes, polyimides, polyamides, polystyrenes, polyolefins, cloth, wool, glass, ceramic, and combinations thereof.

Low-adhesion Backsize (LAB) Coatings

As mentioned above with respect to FIGS. 1 and 2, when the adhesive 14 is coated onto the first major surface 20 of the backing 12, a LAB coating 18 can optionally be coated on the opposite second major surface 22 of the backing 12 to allow the adhesive article 10 to be in the form of a tape that can unwind from itself when wound in a roll or to release when in a pad form. When utilized, the LAB coating composition should be compatible with the adhesive composition and not degrade the adhesive properties of the tape, such as by being transferred to the adhesive composition.

LAB coating compositions may include silicone, alkyl, or fluorochemical constituents, or combinations thereof, as the release imparting component. Useful LAB coating compositions include silicone containing polymers, silicone macromers, such as those described in WO2012091742, and silicone polyurethanes, silicone polyureas and silicone polyurethane/ureas, such as those described in U.S. Pat. Nos. 5,214,119, 5,290,615, 5,750,630, and 5,356,706, and silicone acrylate grafted copolymers described in U.S. Pat. Nos. 5,032,460, 5,202,190, and 4,728,571. Other useful LAB coating compositions include fluorochemical containing polymers such as those described in U.S. Pat. No. 3,318,852, and polymers containing long alkyl side chains such as polyvinyl N-alkyl carbamates (e.g., polyvinyl N-octadecyl carbamates) as described in U.S. Pat. No. 2,532,011, and copolymers containing higher alkyl acrylates (e.g., octadecyl acrylate or behenyl acrylate), such as those described in U.S. Pat. No. 2,607,711, or alkyl methacrylates (e.g., stearyl methacrylate) such as those described in U.S. Pat. Nos. 3,502,497 and 4,241,198, where the alkyl side chain includes from about 16 to 22 carbon atoms.

The following embodiments are intended to be illustrative of the present disclosure and not limiting.

Embodiments

1. An adhesive article comprising:
   a backing having a first major surface and a second major surface opposite the first major surface;
   a primer layer located on the first major surface of the backing, the primer layer being derived from a primer precursor, the primer precursor comprising a compound comprising poly(meth)acrylate functionalities; and
   a silicone-based adhesive located on the primer layer on the first major surface of the backing, such that the primer layer is located between the first major surface of the backing and the adhesive.
2. The adhesive article of embodiment 1, wherein the primer layer and the silicone-based adhesive are covalently bonded together via carbon-carbon bonds.
3. The adhesive article of embodiment 1 or 2, further comprising a low-adhesion backsize coating on the second major surface of the backing.
4. The adhesive article of any of embodiments 1-3, wherein the adhesive has a first adhesion strength on the low-adhesion backsize coating on the second major surface of the backing, wherein the adhesive has a second adhesion strength on the primer layer on the first major surface of the backing, and wherein the first adhesion strength is less than the second adhesion strength.
5. The adhesive article of any of embodiments 1-4, wherein the silicone-based adhesive comprises a nonfunctionalized polysiloxane.
6. The adhesive article of any of embodiments 1-5, wherein the silicone-based adhesive comprises a polydimethylsiloxane (PDMS).
7. The adhesive article of any of embodiments 1-6, wherein the silicone-based adhesive is radiation cured.
8. The adhesive article of embodiment 7, wherein the silicone-based adhesive is electron-beam cured.
9. The adhesive article of embodiment 7, wherein the silicone-based adhesive is ultraviolet radiation-cured.
10. The adhesive article of any of embodiments 1-9, wherein the primer layer has a coating weight on the first major surface of the backing of at least 0.04 g/m².
11. A method of making an adhesive article, the method comprising:
   applying a primer precursor onto a first major surface of a backing, wherein the primer precursor comprises a compound comprising poly(meth)acrylate functionalities;
   irradiating the primer precursor on the backing;
   applying an adhesive on the irradiated primer precursor on the first major surface of the backing; and
   irradiating the adhesive and the irradiated primer precursor on the first major surface of the backing to form a primer layer located between the adhesive and the first major surface of the backing.
12. The method of embodiment 11, wherein irradiating the adhesive and the irradiated primer precursor on the first major surface of the backing to form a primer layer includes forming covalent carbon-carbon bonds between the primer layer and the adhesive.
13. The method of embodiment 11 or 12, wherein irradiating the adhesive and the irradiated primer precursor on the first major surface of the backing to form a primer layer includes irradiating with at least one of electron beam (e-beam) radiation and ultraviolet (UV) radiation.
14. The method of any of embodiments 11-13, wherein irradiating the primer precursor includes irradiating with short wavelength polychromatic ultraviolet radiation.
15. The method of any of embodiments 11-14, further comprising coating a low-adhesion backsize coating on a second major surface of the backing, the second major surface being opposite the first major surface of the backing.
16. The method of any of embodiments 11-15, wherein the adhesive is a silicone-based adhesive.
17. The method of embodiment 16, wherein the silicone-based adhesive comprises a nonfunctionalized polysiloxane.
18. The method of embodiment 16 or 17, wherein the silicone-based adhesive comprises a polydimethylsiloxane (PDMS).
19. The method of any of embodiments 11-18, wherein applying the primer precursor onto the first major surface of the backing includes applying the primer precursor to a coating weight of at least 0.04 g/m².
20. The adhesive article of any of embodiments 1-10 or the method of any of embodiments 11-19, wherein the primer precursor comprises a tri-(meth)acrylate monomer.
21. The adhesive article of any of embodiments 1-10 and 20 or the method of any of embodiments 11-20, wherein the primer precursor comprises a poly(meth)acrylate siloxane.
22. The adhesive article of any of embodiments 1-10 and 20-21 or the method of any of embodiments 11-21, wherein the primer precursor comprises a blend of a poly(meth)acrylate monomer and a poly(meth)acrylate siloxane.
23. The adhesive article of any of embodiments 1-10 and 20-22 or the method of any of embodiments 11-22, wherein the primer precursor is substantially free of an organic solvent.
24. The adhesive article of any of embodiments 1-10 and 20-23 or the method of any of embodiments 11-23, wherein the primer precursor is substantially free of catalysts and initiators.
25. The adhesive article of any of embodiments 1-10 and 20-24 or the method of any of embodiments 11-24, wherein the backing comprises at least one of a foam, a film, a nonwoven, a fabric, and a combination thereof.
26. The adhesive article of any of embodiments 1-10 and 20-25 or the method of any of embodiments 11-25, wherein the film comprises at least one of a polyester, a polyurethane, a polyimide, a polyamide, a polystyrene, a cellulose acetate, a polyolefin, a metallic foil, and a combination thereof.
27. The adhesive article of any of embodiments 1-10 and 20-26 or the method of any of embodiments 11-26, wherein the nonwoven comprises at least one of a polyester, a polyurethane, a polyimide, a polyamide, a polystyrene, a cellulose, a polyolefin, glass fibers, ceramic fibers, and a combination thereof.

28. The adhesive article of any of embodiments 1-10 and 20-27 or the method of any of embodiments 11-27, wherein the fabric comprises at least one of a polyester, a polyurethane, a polyimide, a polyamide, a polystyrene, a polyolefin, cloth, wool, glass, ceramic, and a combination thereof.

29. The adhesive article of any of embodiments 1-10 and 20-28 or the method of any of embodiments 11-28, wherein the backing comprises a polyethylene terephthalate.

30. The adhesive article of any of embodiments 1-10 and 20-29 or the method of any of embodiments 11-29, wherein the backing comprises a polyurethane.

31. The adhesive article of any of embodiments 1-10 and 20-30 or the method of any of embodiments 11-30, wherein the backing comprises a polyethylene blend.

It is to be understood that the invention is not limited in its application to the details of construction and the arrangement of components set forth in the above description or illustrated in the accompanying drawings. The invention is capable of other embodiments and of being practiced or of being carried out in various ways. Also, it is to be understood that the phraseology and terminology used herein is for the purpose of description and should not be regarded as limiting. It is to be further understood that other embodiments may be utilized, and structural or logical changes may be made without departing from the scope of the present disclosure.

The following working examples are intended to be illustrative of the present disclosure and not limiting.

examples

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is distilled water, and all molecular weights are weight average molecular weight.

Raw materials utilized in the sample preparation are shown in Table 1.

TABLE 1

Materials

| Component | Description | Supplier |
| --- | --- | --- |
| RC711 | Acrylated polysiloxanes | Evonik Goldschmidt |
| RC902 | Acrylated polysiloxanes | Evonik Goldschmidt |
| SR444 | Pentaerythriol Tetraacrylate | Sartomer |
| PET-1 | Polyester film, Scotchpak 9753, with a surface treatment as described in U.S. Pat. No. 7,442,442 | 3M |
| PET-2 | Polyester film, Scotchpak 9733 | 3M |
| PU | Polyurethane film, CoTran 9701 | 3M |
| PE | Polyethylene film, CoTran 9722 | 3M |

Test Methods

Adhesion-to-Primer

The adhesion strength of the adhesive to the primer-coated backing interface was tested according to the following procedure:

1) A 4 inch×1 inch (10 cm×2.5 cm) section of 3M Polyester Tape 8403 was laminated to the primer-coated side of Examples E1 to E10 or Comparative Examples C1 to C5;

2) The laminate was rolled down with 2 passes of a 2-kg roller at 12 in/min (30 cm/min.) and allowed to dwell for 5 minutes;

3) The 8403 tape was removed at 12 in/min (30 cm/min.) at 180 degree; and

4) The peel force was obtained using an I-MASS SP 2000 Slip/Peel tester T-133. The peel force is reported in g/25.4 mm.

Coating Weight

The coating weight was measured with Oxford LAB-X 3500.

EXAMPLES

Example 1 (E-1) was prepared by coating the primer precursor of RC711 on PET-1 backing with a 5 roll coater. Each roll speed ratio was adjusted to deliver a 0.042 grams per square meter (gsm) coating to the backing. The coating was then ultra violet irradiated using low pressure mercury amalgam lamps available from Heraeus-Noblelight targeting the emission band of 185 nm in an atmosphere of less than 50 ppm Oxygen with an energy level of 9.6 mj/cm$^2$.

Example 2 (E-2) was prepared by coating the primer precursor of RC711 on PET-1 backing with a 5 roll coater. Each roll speed ratio was adjusted to deliver a 2.1 grams per square meter (gsm) coating to the backing. The coating was then ultra violet irradiated using low pressure mercury amalgam lamps available from Heraeus-Noblelight targeting the emission band of 185 nm in an atmosphere of less than 50 ppm Oxygen with an energy level of 9.6 mj/cm$^2$.

Example 3 (E-3) was prepared by coating the primer precursor of 95/5 RC711/SR444 on PET-1 backing with a 5 roll coater. Each roll speed ratio was adjusted to deliver a 0.15 grams per square meter (gsm) coating to the backing. The coating was then ultra violet irradiated using low pressure mercury amalgam lamps available from Heraeus-Noblelight targeting the emission band of 185 nm in an atmosphere of less than 50 ppm Oxygen with an energy level of 9.6 mj/cm$^2$.

Example 4 (E-4) was prepared by coating the primer precursor of 90/10 RC711/SR444 on PET-1 backing with a 5 roll coater. Each roll speed ratio was adjusted to deliver a 0.15 grams per square meter (gsm) coating to the backing. The coating was then ultra violet irradiated using low pressure mercury amalgam lamps available from Heraeus-Noblelight targeting the emission band of 185 nm in an atmosphere of less than 50 ppm Oxygen with an energy level of 9.6 mj/cm$^2$.

Example 5 (E-5) was prepared by coating the primer precursor of 85/15 RC711/SR444 on PET-1 backing with a 5 roll coater. Each roll speed ratio was adjusted to deliver a 0.15 grams per square meter (gsm) coating to the backing. The coating was then ultra violet irradiated using low pressure mercury amalgam lamps available from Heraeus-Noblelight targeting the emission band of 185 nm in an atmosphere of less than 50 ppm Oxygen with an energy level of 9.6 mj/cm$^2$.

Example 6 (E-6) was prepared by coating the primer precursor of 70/30 RC902/RC711 on PET-2 backing with a 5 roll coater. Each roll speed ratio was adjusted to deliver a 0.097 grams per square meter (gsm) coating to the backing. The coating was then ultra violet irradiated using low pressure mercury amalgam lamps available from Heraeus-Noblelight targeting the emission band of 185 nm in an atmosphere of less than 50 ppm Oxygen with an energy level of 9.6 mj/cm$^2$.

Example 7 (E-7) was prepared by coating the primer precursor of 95/5 RC711/SR444 on PU backing with a 5 roll coater. Each roll speed ratio was adjusted to deliver a 0.15 grams per square meter (gsm) coating to the backing. The coating was then ultra violet irradiated using low pressure mercury amalgam lamps available from Heraeus-Noblelight targeting the emission band of 185 nm in an atmosphere of less than 50 ppm Oxygen with an energy level of 9.6 mj/cm$^2$.

Example 8 (E-8) was prepared by coating the primer precursor of 95/5 RC711/SR444 on PU backing with a 5 roll coater. Each roll speed ratio was adjusted to deliver a 3.8 grams per square meter (gsm) coating to the backing. The coating was then ultra violet irradiated using low pressure mercury amalgam lamps available from Heraeus-Noblelight targeting the emission band of 185 nm in an atmosphere of less than 50 ppm Oxygen with an energy level of 9.6 mj/cm$^2$.

Example 9 (E-9) was prepared by coating the primer precursor of 95/5 RC711/SR444 on PU backing with a 5 roll coater. Each roll speed ratio was adjusted to deliver a 0.25 grams per square meter (gsm) coating to the backing. The coating was then ultra violet irradiated using low pressure mercury amalgam lamps available from Heraeus-Noblelight targeting the emission band of 185 nm in an atmosphere of less than 50 ppm Oxygen with an energy level of 9.6 mj/cm$^2$.

Example 10 (E-10) was prepared by coating the primer precursor of RC711 on a PE backing with a 5 roll coater. Each roll speed ratio was adjusted to deliver a 0.065 grams per square meter (gsm) coating to the backing. The coating was then ultra violet irradiated using low pressure mercury amalgam lamps available from Heraeus-Noblelight targeting the emission band of 185 nm in an atmosphere of less than 50 ppm Oxygen with an energy level of 9.6 mj/cm$^2$.

The comparative example 1 (C-1) was PET-1 backing without any primer layer.

The comparative example 2 (C-2) was PET-2 backing without any primer layer.

The comparative example 3 (C-3) was PU backing without any primer layer.

The comparative example 4 (C-4) was PE backing without any primer layer.

Results

Results for the adhesion-to-primer test for Examples E1-E10 and Comparative Examples C1-C4 are reported in Table. 2.

TABLE 2

Adhesion Results

| Sample | Backing | Primer Composition | (gsm) | Adhesion to Primer oz/in (kg/m) |
|---|---|---|---|---|
| Examples | | | | |
| E-1 | PET-1 | RC711 | 0.042 | 15.5 (17.3) |
| E-2 | PET-1 | RC711 | 2.1 | 15.7 (17.5) |
| E-3 | PET-1 | 95/5 RC711/SR444 | 0.15 | 18.2 (20.3) |
| E-4 | PET-1 | 90/10 RC711/SR444 | 0.15 | 18.4 (20.5) |
| E-5 | PET-1 | 85/15 RC711/SR444 | 0.15 | 14.7 (16.4) |
| E-6 | PET-2 | 70/30 RC902/RC711 | 0.097 | 13.6 (15.2) |
| E-7 | PU | 95/5 RC711/SR444 | 0.15 | 10.7 (11.9) |
| E-8 | PU | 95/5 RC711/SR444 | 3.8 | 15.0 (16.7) |
| E-9 | PU | 95/5 RC711/SR444 | 0.25 | 15.3 (17.1) |
| E-10 | PE | RC711 | 0.065 | 10.5 (11.7) |
| Comparatives | | | | |
| C-1 | PET-1 | No primer coating | | 6.8 (7.6) |
| C-2 | PET-2 | No primer coating | | 6.4 (7.1) |
| C-3 | PU | No primer coating | | 5.3 (5.9) |
| C-4 | PE | No primer coating | | 6.3 (7.0) |

The embodiments described above and illustrated in the figures are presented by way of example only and are not intended as a limitation upon the concepts and principles of the present disclosure.

All references and publications cited herein are expressly incorporated herein by reference in their entirety into this disclosure.

Various features and aspects of the present disclosure are set forth in the following claims.

What is claimed is:

1. An adhesive article comprising:
   a backing having a first major surface and a second major surface opposite the first major surface;
   a primer layer located on the first major surface of the backing, the primer layer being derived from a primer precursor, the primer precursor comprising a (meth) acrylate-functional siloxane oligomer or polymer having three or more pendant (meth)acrylate functional end groups, and wherein the primer precursor is free of Si—O—C covalent bonds; and
   a silicone-based adhesive located on the primer layer on the first major surface of the backing, such that the primer layer is located between the first major surface of the backing and the adhesive.

2. The adhesive article of claim 1, wherein the primer layer and the silicone-based adhesive are covalently bonded together via carbon-carbon bonds.

3. The adhesive article of claim 1, further comprising a low-adhesion backsize coating on the second major surface of the backing.

4. The adhesive article of claim 3, wherein the adhesive has a first adhesion strength on the low-adhesion backsize coating on the second major surface of the backing, wherein the adhesive has a second adhesion strength on the primer layer on the first major surface of the backing, and wherein the first adhesion strength is less than the second adhesion strength.

5. The adhesive article of claim 1, wherein the silicone-based adhesive comprises a nonfunctionalized polysiloxane.

6. The adhesive article of claim 1, wherein the primer precursor further comprises a tri-(meth)actylate monomer.

7. The adhesive article of claim 1, wherein the primer precursor is substantially free of an organic solvent.

8. The adhesive article of claim 1, wherein the primer precursor is substantially free of catalysts and initiators.

9. The adhesive article of claim 1, wherein the backing comprises at least one of a polyethylene terephthalate and a polyurethane.

10. The adhesive article of claim 1, wherein the primer precursor comprises telechelic (meth)acrylate functional end groups.

* * * * *

UNITED STATES PATENT AND TRADEMARK OFFICE
CERTIFICATE OF CORRECTION

PATENT NO. : 10,617,786 B2  
APPLICATION NO. : 15/533735  
DATED : April 14, 2020  
INVENTOR(S) : Bruce Kluge Page 1 of 1

It is certified that error appears in the above-identified patent and that said Letters Patent is hereby corrected as shown below:

In the Specification

<u>Column 6</u>
Line 28      Delete "polylsiloxane" and insert -- polysiloxane --, therefor.
Line 54      Delete "polylsiloxane" and insert -- polysiloxane --, therefor.

<u>Column 7</u>
Line 1      Delete "tetr(" and insert -- tetra( --, therefor.

<u>Column 13</u>
Line 51      Delete "Pentaerythriol" and insert -- Pentaerythritol --, therefor.

In the Claims

<u>Column 16</u>
Line 55      Claim 6, delete ")actylate" and insert -- )acrylate --, therefor.

Signed and Sealed this  
Twentieth Day of April, 2021

Drew Hirshfeld  
*Performing the Functions and Duties of the*  
*Under Secretary of Commerce for Intellectual Property and*  
*Director of the United States Patent and Trademark Office*